(12) United States Patent
Isozaki et al.

(10) Patent No.: US 6,771,364 B2
(45) Date of Patent: Aug. 3, 2004

(54) SURFACE INSPECTING APPARATUS

(75) Inventors: Hisashi Isozaki, Tokyo (JP); Michihiro Yamazaki, Tokyo (JP); Hiroshi Yoshikawa, Tokyo (JP); Yoichiro Iwa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 10/225,455

(22) Filed: Aug. 22, 2002

(65) Prior Publication Data

US 2004/0036865 A1 Feb. 26, 2004

(51) Int. Cl.$^7$ .............................................. G01B 11/00
(52) U.S. Cl. ................................................. 356/237.2
(58) Field of Search .......................... 356/237.1–237.6; 250/559.4, 559.41, 559.42, 559.45

(56) References Cited

U.S. PATENT DOCUMENTS

| | | | | |
|---|---|---|---|---|
| 6,587,192 B2 | * | 7/2003 | Isozaki et al. | ............ 356/237.2 |
| 2001/0035951 A1 | * | 11/2001 | Isozaki et al. | ............ 356/237.3 |
| 2002/0021438 A1 | * | 2/2002 | Isozaki et al. | ............ 356/237.5 |

* cited by examiner

Primary Examiner—Michael P. Stafira
(74) Attorney, Agent, or Firm—Foley & Lardner LLP (57) ABSTRACT

A surface inspection apparatus comprises: a light source section that emits a first luminous flux and a second luminous flux; an irradiation optical system that irradiates the first luminous flux and the second luminous flux on the surface of the film-coated inspection subject; a displacement section that relatively displaces the film-coated inspection subject and an irradiation luminous flux from the irradiation optical system; a light-receiving optical system that receives scattered light generated from the inspection subject on the film-coated inspection subject after irradiation of the first luminous flux from the irradiation optical system and scattered light generated from the inspection subject on the film-coated inspection subject after irradiation of the second luminous flux from the irradiation optical system; a first light-receiving section that transforms the scattered light of the first luminous flux received by the light-receiving optical system into a first light reception signal; a second light-receiving section that transforms the scattered light of the second luminous flux received by the light-receiving optical system into a second light reception signal; and a sensitivity stabilizing section that synthesizes the first light reception signal and the second light reception signal to form a signal for sampling.

11 Claims, 7 Drawing Sheets

FILM THICKNESS AND REFLECTIVITY
WHEN 3 WAVELENGTHS ARE USED    SiO₂

SURFACE INSPECTING APPARATUS

BACKGROUND OF THE INVENTION

1. Field of the Invention

The present invention relates to a surface inspection apparatus to inspect an inspection subject (such as a particle and a flaw) on the surface of a film-coated wafer or other film-coated inspection subjects.

2. Related Art

Conventionally, when inspecting the surface of a transmissive film, a metal film, or the like of the film-coated wafer, a luminous flux has been made incident with a low angle to detect a particle on the surface. However, in surface inspection of the film-coated wafer on which the transmissive film was formed, reflectivity has varied depending on a film thickness and a material of the transmissive film and it has not been possible to ensure detection sensitivity at a constant level when the film thickness was not uniform.

When the film thickness was fixed, a plane of polarization has been switched in P-polarized light, S-polarized light, circular polarized light, and PS-polarized light to find optimum polarization conditions, and thus the particle has been detected.

However, in recent years, a CMP (chemical mechanical polishing) process has been introduced in processing of the film-coated wafer with microfabrication thereof. Once the processing such as the CMP was introduced in the processing of the film-coated wafer, the thickness of a film formed on the film-coated wafer varied in each wafer and the thickness scarcely has become uniform always.

The film thickness varies for each wafer when the CMP is applied for the film-coated wafer on which the transmissive film has been formed. Due to the variation of reflectivity caused by the varied film thickness, it has become difficult to ensure detection sensitivity of a constant level in the surface inspection of the film-coated wafer after the CMP processing. There are cases where particle detection sensitivity drastically reduces in the surface inspection of the film-coated wafer on which the transmissive film has been formed depending on an inspection position.

However, the CMP processing is essential to the microfabrication technology.

In addition, there exists a demand for an apparatus that can detect the particle such as a flaw and a CMP residue with good sensitivity.

Moreover, wafers of a new structure that pursue low electric consumption and high-speed operation such as an SOI wafer, for example, have been available. These wafers have a structure of a plurality of films by a thin Si film, $SiO_2$ film and an Si base, and there have been cases of causing interference to widely vary sensitivity due to the relationship with an incident wavelength depending on the inspection position of the wafer surface.

SUMMARY OF THE INVENTION

The object of the present invention is to provide a surface inspection apparatus to perform surface inspection for a film-coated wafer or other film-coated inspection subjects, that is, inspection for a particle, a flaw, or the like, with stable sensitivity.

The present invention is one that has improved a surface inspection apparatus to inspect an inspection subject (such as a particle and a flaw) on the surface of the film-coated wafer or the other film-coated inspection subjects.

In a typical example of the present invention, the surface inspection apparatus comprises: a light source section that emits a first luminous flux and a second luminous flux; an irradiation optical system that irradiates the first luminous flux and the second luminous flux on the surface of the film-coated inspection subject; a displacement section that relatively displaces the film-coated inspection subject and an irradiation luminous flux from the irradiation optical system; a light-receiving optical system that receives scattered light generated from the inspection subject on the film-coated inspection subject after irradiation of the first luminous flux from the irradiation optical system and scattered light generated from the inspection subject on the film-coated inspection subject after irradiation of the second luminous flux from the irradiation optical system; a first light-receiving section that transforms the scattered light of the first luminous flux received by the light-receiving optical system into a first light reception signal; a second light-receiving section that transforms the scattered light of the second luminous flux received by the light-receiving optical system into a second light reception signal; and a sensitivity stabilizing section that synthesizes the first light reception signal and the second light reception signal to form a signal for sampling.

Preferably, a first characteristic of the first luminous flux and a second characteristic of the second luminous flux are wavelengths or polarization component of the luminous fluxes. The sensitivity stabilizing section selects either one of the first light reception signal and the second light reception signal for every inspection position of the film-coated inspection subject surface, and synthesizes the first light reception signal and the second light reception signal. Further, the sensitivity stabilizing section selects a light reception signal from which a detection sensitivity closer to a desired detection sensitivity has been obtained out of the first light reception signal and the second light reception signal for every inspection position of the film-coated inspection subject surface, and synthesizes the first light reception signal and the second light reception signal. Furthermore, the sensitivity stabilizing section selects a light reception signal from which a higher sensitivity has been obtained out of the first light reception signal and the second light reception signal for every inspection position of the film-coated inspection subject surface, and synthesizes the first light reception signal and the second light reception signal.

Preferably, a combination of the first luminous flux and the second luminous flux is a combination of luminous fluxes such that either the first light reception signal or the second light reception signal is obtained with predetermined detection sensitivity for every inspection position of the film-coated inspection subject surface.

PREFERRED EMBODIMENTS OF THE INVENTION

Figure 1:
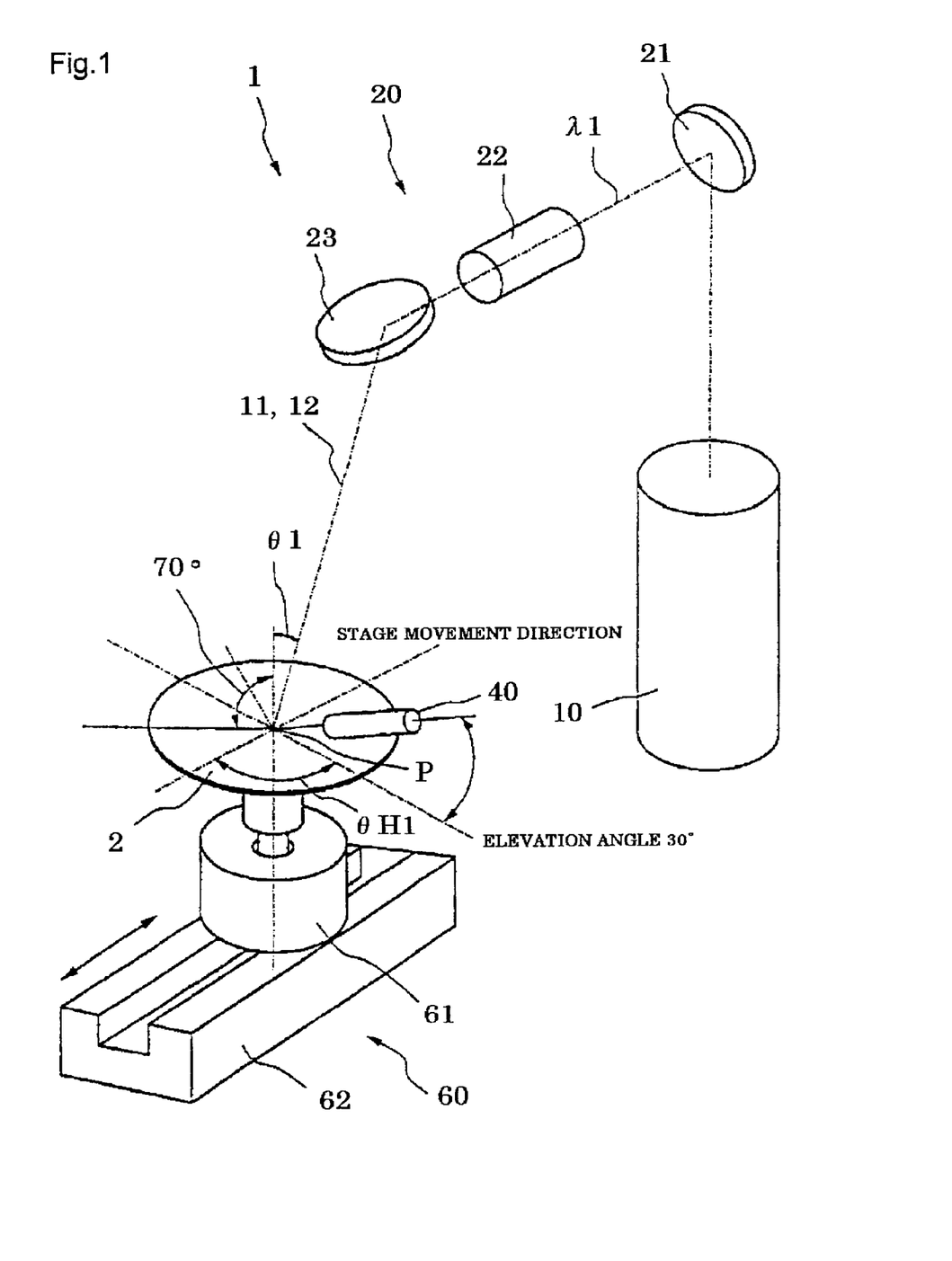
FIG. 1 is a schematic arrangement view of a primary optical component of a surface inspection apparatus according to one preferred embodiment of the present invention.

FIG. 1 is the schematic arrangement view of the primary optical component of the surface inspection apparatus according to one preferred embodiment of the present invention.

A surface inspection apparatus 1 has: a light source section 10 such as a laser tube that emits at least a luminous flux 11 having a first wavelength $\lambda 1$ and a luminous flux 12 having a second wavelength $\lambda 2$ different from $\lambda 1$; an irradiation optical system 20 that irradiates the luminous flux 11 having the first wavelength $\lambda 1$ and the luminous flux 12 having the second wavelength $\lambda 2$ from the light source section 10 on an inspection point P of the surface of a film-coated semiconductor wafer 2 as the film-coated inspection subject in a first irradiation angle $\theta 1$; a light-receiving optical system 40 that receives the scattered light from the inspection point P of the surface of the semiconductor wafer 2, which is caused by the luminous fluxes 11, 12 irradiated from the irradiation optical system 20; and a displacement section 60 capable of moving the film-coated semiconductor wafer 2 as the film-coated inspection subject rotatably and linearly for the irradiation luminous flux 11 from the irradiation optical system 20 in a relative manner. An elevation angle of the light-receiving optical system 40 in FIG. 1 is 30°.

Description will be made for the light source section 10. The light source section 10 emits at least the luminous flux 11 having the first wavelength and the luminous flux 12 having the second wavelength different from the first wavelength. Various kinds of light sources that emit luminous fluxes having different wavelengths can be used as the light source section 10. For example, a multi-line laser where one light source emits luminous fluxes having a plurality of wavelengths or one that synthesizes luminous fluxes from a plurality of light sources, which emit luminous fluxes having different wavelengths, with a half mirror to form one beam can be adopted.

When a luminous flux having an unnecessary wavelength occurs in the case of adopting the multi-line laser, the luminous fluxes are made to pass a band-pass filter that passes the first wavelength and the second wavelength, and thus only a luminous flux having a necessary wavelength can be brought out.

When a plurality of light sources that emit luminous fluxes of different wavelengths are used, a plurality of the luminous fluxes are synthesized by the half mirror or the like to form one beam.

In the case of using an argon ion laser as the light source section 10 in the example of FIG. 1, the wavelength of 488 nm and the wavelength of 514.5 nm can be selected. The direction of the luminous flux 11 having the first wavelength and the luminous flux 12 having the second wavelength, which have been emitted from the light source section 10, is changed by a first mirror 21, and the luminous fluxes are irradiated on the irradiation point P on the surface of the film-coated inspection subject with the first irradiation angle $\theta 1$ via a first irradiation lens group 22 and a second mirror 23.

If the inspection subject, that is, a particle or the like, exists on the inspection point P, the scattered light occurs according to a predetermined directivity when the irradiation luminous flux is irradiated on the subject. The first irradiation angle $\theta 1$ is set using a normal line direction of the film-coated inspection subject 2 as a reference.

In the embodiment of FIG. 1, size of the first wavelength $\lambda 1$ and the second wavelength $\lambda 2$ can be arbitrarily selected.

Next, the light-receiving optical system 40 will be described. The light-receiving optical system 40 is provided to receive the above-described scattered light. The light-receiving optical system 40 receives the scattered light from the inspection point P of the surface of the film-coated semiconductor wafer 2, which is caused by the luminous fluxes 11, 12 irradiated from the irradiation optical system 20. A first light-receiving horizontal angle $\theta H1$ (90° for example) in a first light-receiving direction is measured using a reflection direction of the irradiation luminous fluxes 11, 12 from the irradiation optical system 20, when the fluxes have made a specular reflection on the film-coated inspection subject 2, as a reference. A light-receiving elevation angle in the first light-receiving direction is set to 30°, for example.

Figure 2:
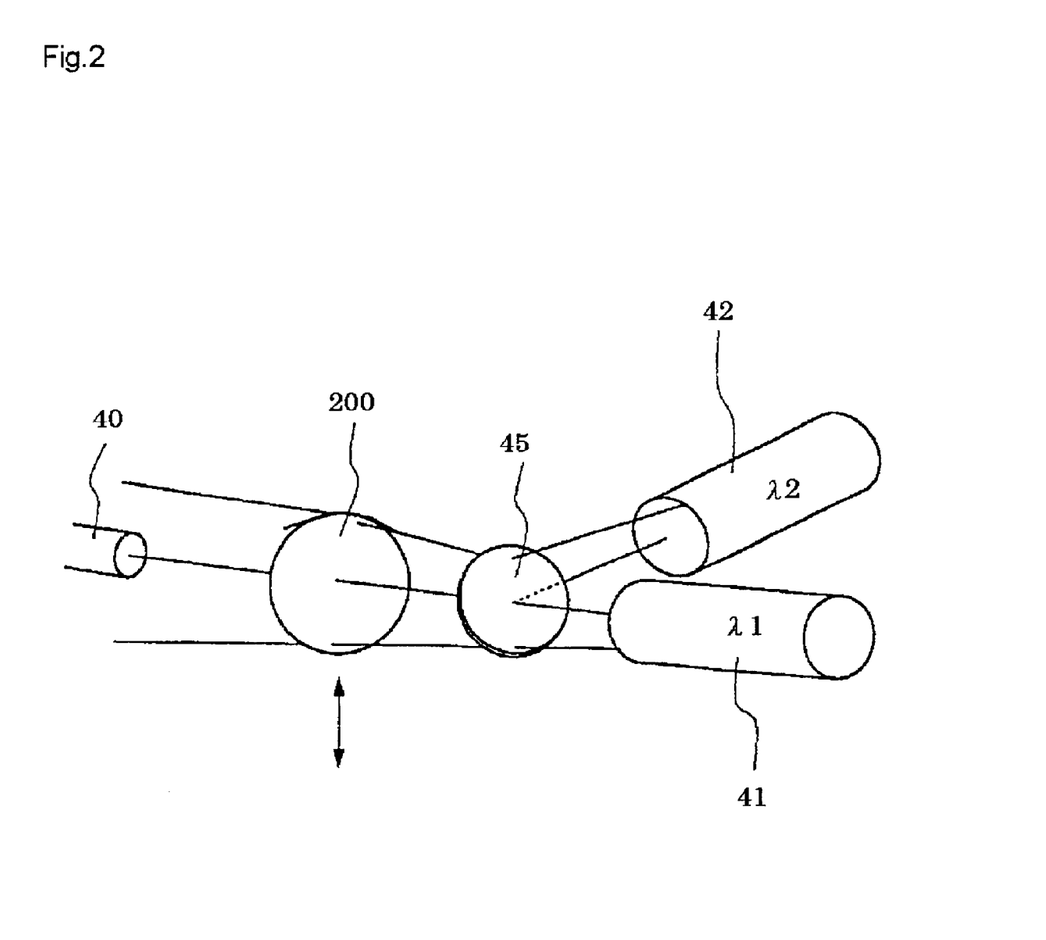
FIG. 2 is a detail view of a light-receiving optical system.

As shown in FIG. 2, the luminous flux received by the light-receiving optical system 40 passes an ND filter 200 movably arranged in the arrow directions to be inserted in or withdrawn from a light reception optical path, and then is separated into the luminous flux having the first wavelength $\lambda 1$ and the luminous flux having the second wavelength $\lambda 2$ by a dichroic mirror 45. Then, a first light-receiving section 41 receives the scattered light having the first wavelength $\lambda 1$ received by the light-receiving optical system 40 and transforms it into the first light reception signal. A second light-receiving section 42 receives the scattered light having the second wavelength $\lambda 2$ received by the light-receiving optical system 40 and transforms it into the second light reception signal. It is preferable that the first light-receiving section 41 and the second light-receiving section 42 be a light-receiving device such as a photo-multiplier.

The displacement section 60 will be described. The displacement section 60 essentially consists of a rotating displacement section 61 that displaces the film-coated inspection subject 2 in a rotating manner, and a linear displacement section 62 that linearly displaces the film-coated inspection subject 2. The linear displacement section 62 is moved by a predetermined ratio of the width of luminous flux for one rotation displacement of the rotating displacement section 61, and thus the irradiation light from the irradiation optical system 20 spirally scans the film-coated inspection subject 2 from edge to edge.

The present invention is not limited to the above-described scanning method, but the irradiation luminous flux may perform linear scanning by a polygon mirror or the like instead of the rotating displacement.

In the embodiment of FIG. 1, the rotating displacement section 61 essentially consists of a rotation motor that rotates a rotating table, and the linear displacement section 62 essentially consists of a sliding movement section that linearly moves the rotating motor. The sliding movement section, with its movement, displaces the inspection subject 2 such that the irradiation position of the irradiation luminous fluxes 11, 12 from the irradiation optical system 20 passes the center thereof and it crosses in a diameter direction.

Figure 3:
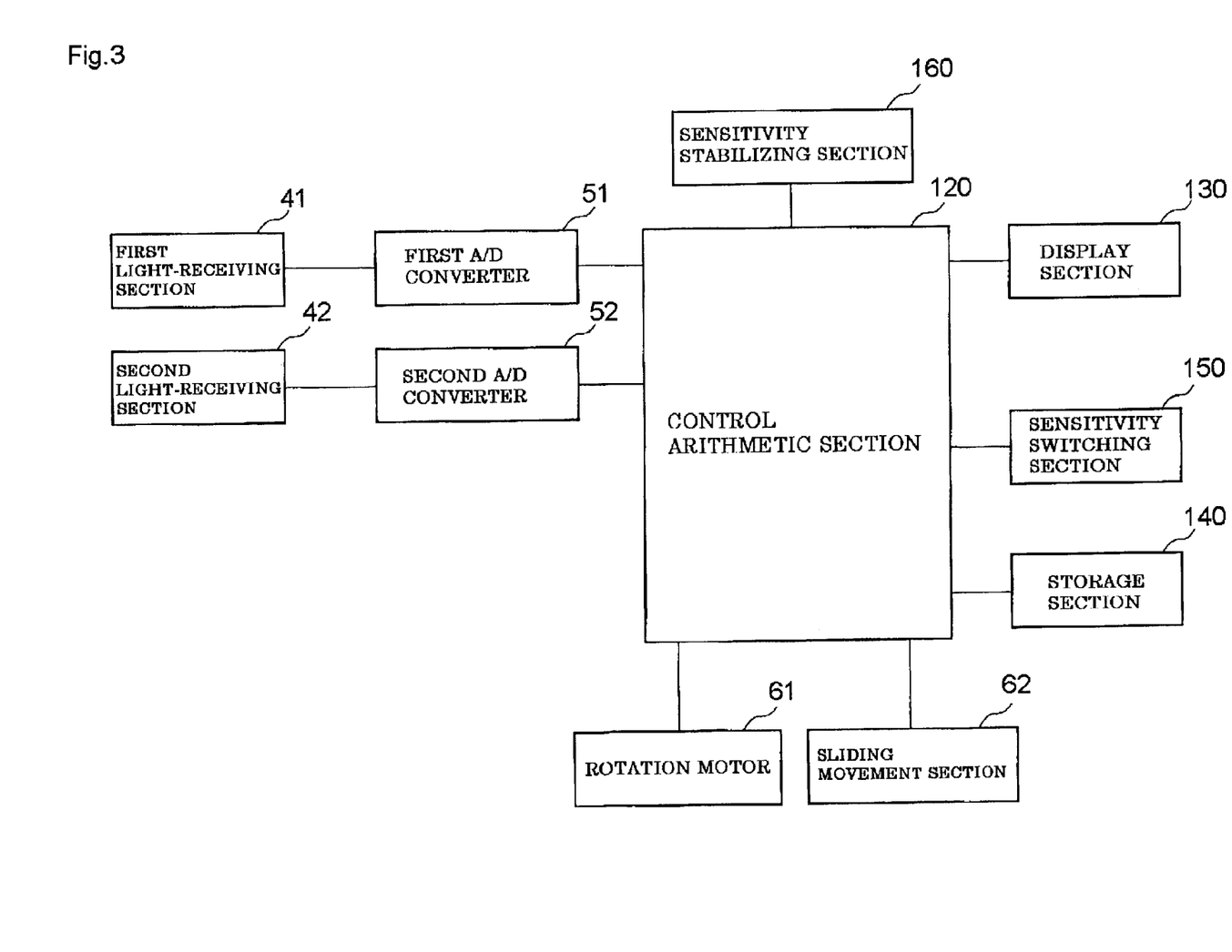
FIG. 3 is a block diagram of the surface inspection apparatus shown in FIG. 1.

FIG. 3 is the block diagram of the surface inspection apparatus shown in FIG. 1.

The first light reception signal from the first light-receiving section and the second light reception signal from the second light-receiving section are transformed into digital signals by a first A/D converter 51 and a second A/D converter 52 respectively, and then are sent to a control arithmetic section 120, which serves as a signal processing section, to perform a predetermined signal processing. The control arithmetic section 120 performs a predetermined signal processing (described later), where it displays an inspection result and a processing result on a display section 130, stores them in a storage section 140, and reads out the contents stored.

Further, the control arithmetic section 120 forms the signal for sampling described later in a sensitivity stabilizing section 160.

Furthermore, the sensitivity stabilizing section 160 also serves as a detection signal forming section. The control arithmetic section 120 controls the rotation motor of the rotating displacement section 61 or the sliding movement section of the linear displacement section 62, or controls a sensitivity switching section 150 for the first light-receiving section 41 and the second light-receiving section 42.

The sensitivity switching section 150 moves the ND filter 200 in the arrow directions of FIG. 2, and switches sensitivity by inserting the ND filter 200 in a light reception window for the first light-receiving section 41 and the second light-receiving section 42 to reduce sensitivity or by withdrawing the ND filter 200 from the light reception window to increase sensitivity.

When the first light-receiving section 41 and the second light-receiving section 42 are formed of the photomultiplier, adjustment of a voltage applied to the sections can also switch sensitivity.

Next, description will be made for formation of the signal for sampling based on the first light reception signal and the second light reception signal. Generally, it is known that the transmissive film and particle detection sensitivity approximate the relationship between the reflectivity and the film thickness. In other words, the higher the reflectivity, the higher the detection sensitivity.

Figure 4:
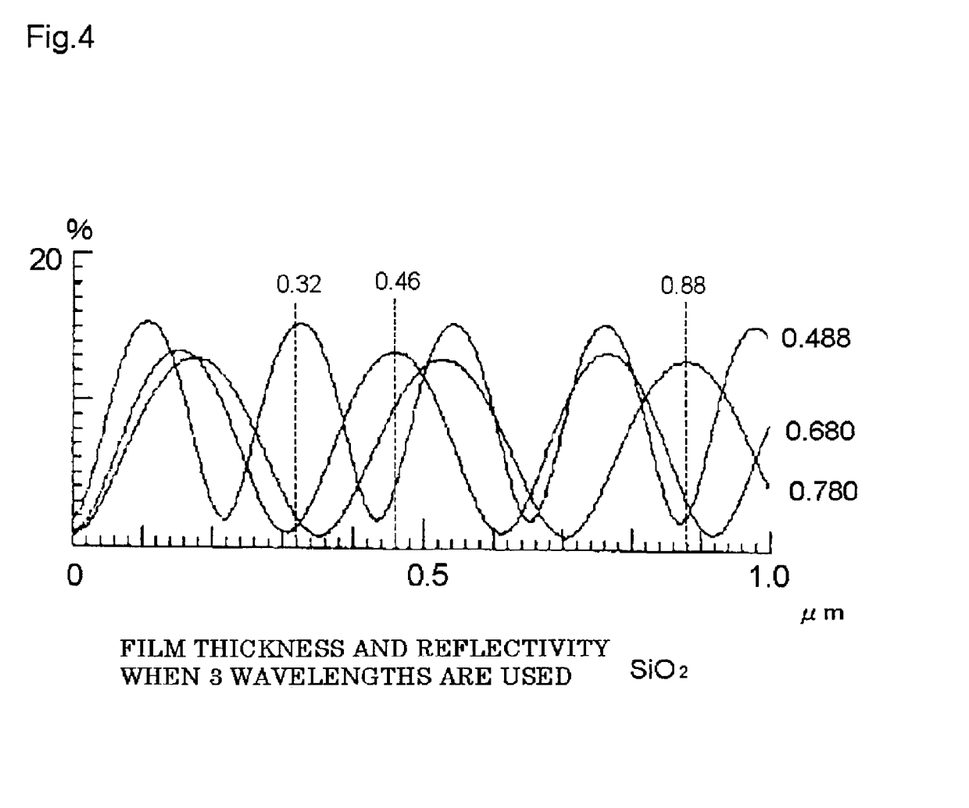
FIG. 4 is a graph showing a relationship between the film thickness and the reflectivity of the transmissive film when luminous fluxes having 3 wavelengths are irradiated on the film-coated wafer.

FIG. 4 is the graph showing the relationship between the film thickness and the reflectivity of the transmissive film when luminous fluxes having 3 wavelengths of 0.488 μm, 0.680 μm and 0.780 μm have been irradiated on the transmissive film coated wafer.

It is understood that periods of peaks having large reflectivity and valleys having small reflectivity varies depending on the wavelength. For this reason, when a few luminous fluxes having different wavelengths are selectively combined and are made incident coaxially and simultaneously to perform inspection, number of places having sensitivity significantly different from other places are reduced comparing to the case of making a luminous flux having one wavelength incident to perform inspection. In short, the reflectivity is maintained at a constant level. Specifically, a case is assumed where the film-coated wafers provided with the transmissive films having the film thickness of 0.32 μm, 0.46 μm and 0.88 μm are mixed in a line. In this case, light having the wavelength of 0.488 μm is selected when measuring the film-coated wafer provided with the transmissive film of 0.32 μm, light having the wavelength of 0.680 μm is selected when measuring the film-coated wafer provided with the transmissive film of 0.46 μm, and light having the wavelength of 0.780 μm is selected when measuring the film-coated wafer provided with the transmissive film of 0.880 μm, and thus measurement can be performed with appropriate sensitivity in measuring a wafer of any film thickness.

Table 1 shows compatibility between the film thickness and the wavelength selected. In Table 1, ⊙ (double circle), ○ (single circle), and – (minus) respectively show optimum, good, and unfavorable.

TABLE 1

| Film Thickness (μm) | Wavelength (μm) | | |
| --- | --- | --- | --- |
|  | 0.488 | 0.680 | 0.780 |
| 0.32 | ⊙ | — | — |
| 0.46 | — | ⊙ | — |
| 0.88 | — | — | ⊙ |

When the luminous flux having such wavelength is selected, sensitivity is prevented from becoming unstable due to the changes of the film thickness of the transmissive film, and sensitivity is stabilized.

The first light reception signal received by the light-receiving section 41 is transformed from an analog signal into a digital signal by the first A/D converter 51. The second light reception signal received by the light-receiving section 42 is transformed from the analog signal into the digital signal by the second A/D converter 52.

In the first light reception signal and the second light reception signal transformed into the digital signals, the sensitivity stabilizing section 160 compares the detection sensitivity for every inspection position of the film-coated wafer surface. Then, the sensitivity stabilizing section 160 adopts a value of a light reception signal having higher detection sensitivity for every inspection position of the film-coated wafer surface, and forms the signal for sampling in order to sample the inspection subject.

Figure 5:
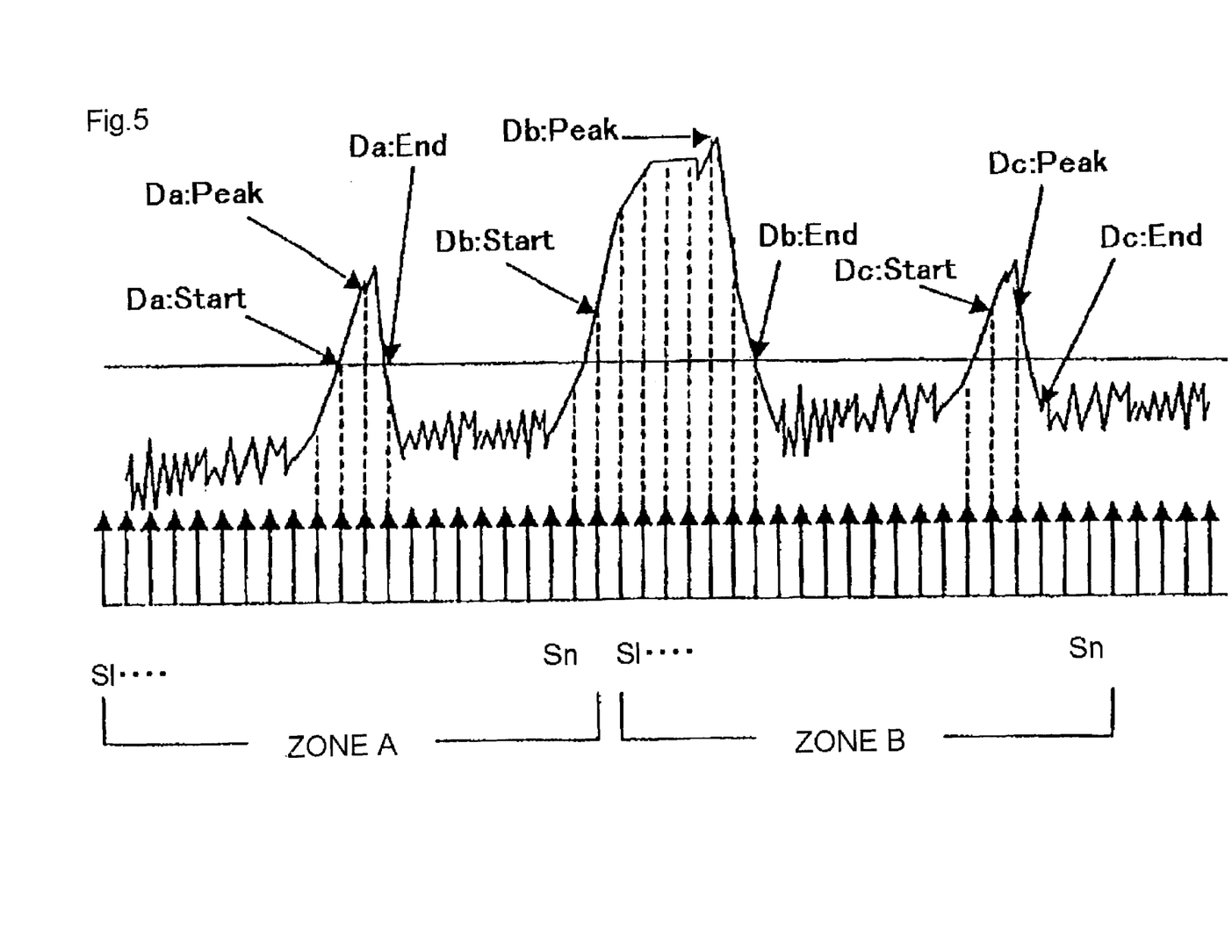
FIG. 5 is a graph showing a structure of inspection subject data in the signal for sampling.
Figure 6:
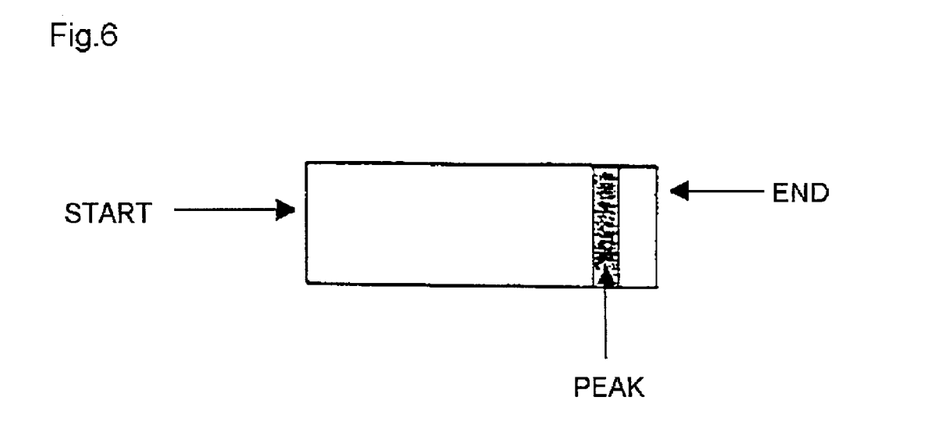
FIG. 6 is an exemplary view of the inspection subject data.

Next, sampling of the inspection subject using the signal for sampling will be described. FIG. 5 is the graph showing the structure of the inspection subject data in the signal for sampling. FIG. 6 is the exemplary view of the inspection subject data.

In the signal for sampling, when the detection light is made to scan in a predetermined direction, if a scattering signal from the inspection subject exceeds a threshold signal (horizontally shown in a solid line in FIG. 5) of the inspection subject, it is stored as a starting coordinates (Start), and then, if the scattering signal from the inspection subject goes below the threshold signal, it is stored as an ending coordinates (End), and a point having the largest scattering signal from the inspection subject between the starting coordinates and the ending coordinates is stored as a peak level value (Peak). Based on the inspection subject data formed of the starting coordinates (Start), the peak level value (Peak), and the ending coordinates (End), the inspection subject on the surface of the film-coated inspection subject is identified.

In FIG. 5, since the inspection subjects of Da, Db, and Dc are identified, the number of the inspection subjects is 3. In this case, data in zones A and B have no connection with the number of the inspection subjects and the number of the inspection subjects is counted in 3.

As described, the signal for sampling used in sampling the inspection subject is formed based on the light reception signal from which constant detection sensitivity has been obtained and the inspection subject data is sampled from the signal for sampling, and thus the inspection subject such as particles and flaws can be identified based on the inspection subject data obtained with stable sensitivity. For example, it is possible to measure particles and flaws occurred in the CMP process or the like for the film-coated wafer with good accuracy.

Therefore, influence that the film thickness of the transmissive film of the film-coated wafer, which is given to the detection sensitivity for the inspection subject, is restricted, and the surface inspection of the film-coated wafer can be performed with stable sensitivity.

The present invention is not limited to the foregoing embodiments.

The luminous flux made incident on the surface of the film-coated inspection subject may be 3 or more luminous fluxes having different wavelengths with each other.

Figure 7:
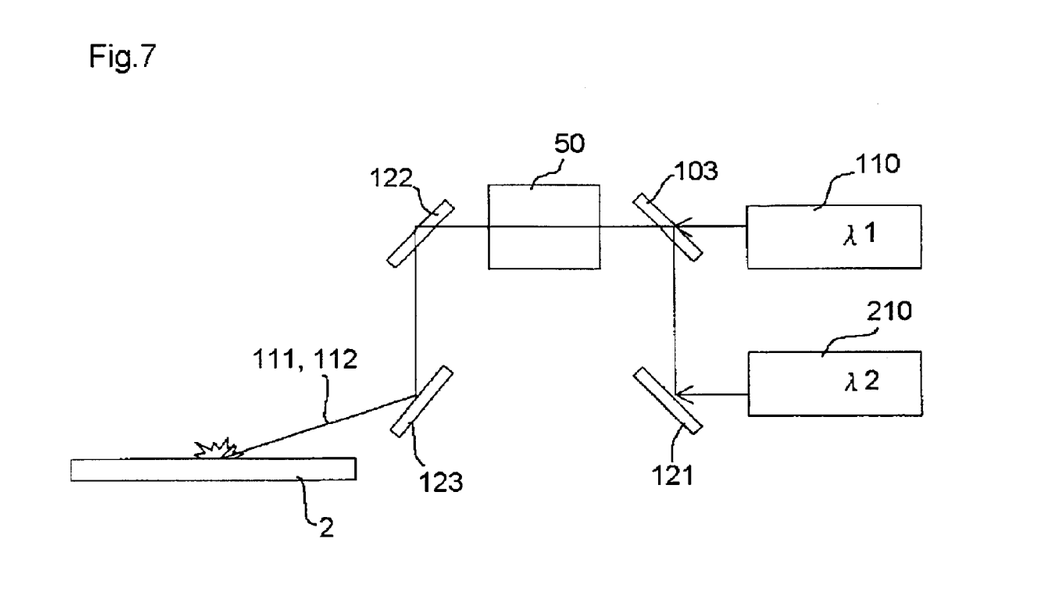
FIG. 7 is a block diagram of a system having a plurality of light sources that emit luminous fluxes of different wavelengths.
Figure 8:
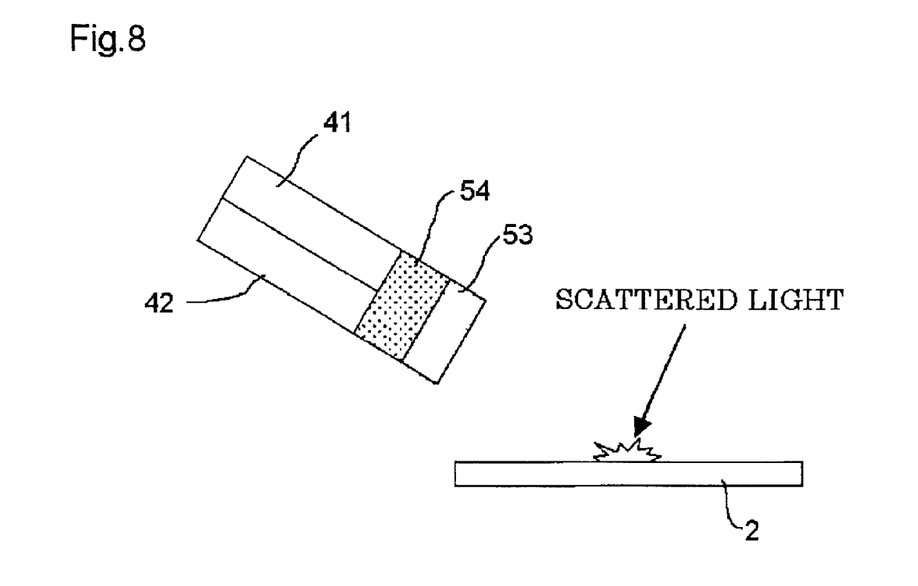
FIG. 8 is a block diagram of a detection system used in the system shown in FIG. 7.

Further, a plurality of light source sections 110, 210 that emit luminous fluxes having different wavelengths as shown in FIG. 7 may be used as the light source section 10 shown in FIG. 1. In this case, the light source sections 110, 210 can severally make ON/OFF control. A luminous flux 111 having the wavelength λ1 emitted from the light source section 110 passes a half mirror 103. A luminous flux 112 having the wavelength λ2 emitted from the light source section 210 is reflected by a mirror 121. The luminous flux 112 having the wavelength λ2 reflected by the mirror 121 is reflected by the half mirror 103. The luminous flux 111 having the wavelength λ1 and the luminous flux 112 having the wavelength λ2 pass a lens unit 50. The lens unit 50 has a beam shaping function or a polarized light selecting function. The luminous flux 111 having the wavelength λ1 that has passed the lens unit 50 is reflected by a mirror 122 and a mirror 123 and irradiated on the film-coated inspection subject 2. The luminous flux 112 having the wavelength λ2 that has passed the lens unit 50 is reflected by the mirror 122 and the mirror 123 and irradiated on the film-coated inspection subject 2. The scattered light generated after the luminous fluxes 111, 112 were irradiated on the film-coated inspection subject 2 is detected by a detection system essentially consists of a lens 53, a wavelength discriminating device 54, and light-receiving devices 41, 42 as shown in FIG. 8.

Furthermore, a plurality of luminous fluxes irradiated in the present invention may be irradiated not only from the same direction but also irradiated from different directions in the same irradiation angle.

Moreover, it is also possible that a plurality of luminous fluxes irradiated are made incident in different angles with each other. In this case, the light-receiving optical system receives the scattered light for every luminous flux having a different wavelength, and can detect the inspection subject by the irradiation luminous flux having an arbitrary incident angle.

Further, the luminous flux used in the present invention may be luminous fluxes having different polarization component with each other instead of a plurality of luminous fluxes having different wavelengths with each other. In performing the surface inspection of the film-coated inspection subject by using the luminous fluxes having different polarization component with each other, the detection system uses the polarizing plate.

Figure 9:
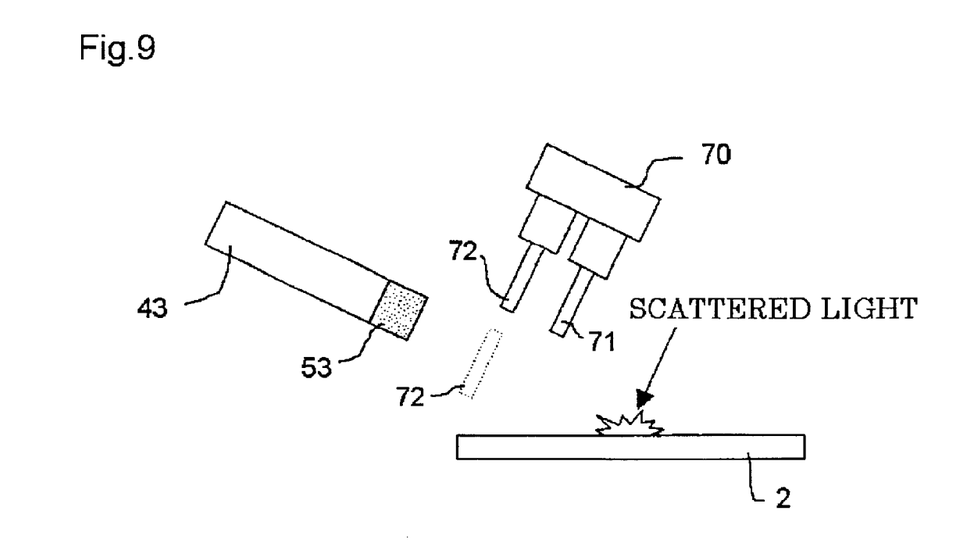
FIG. 9 is a view showing a detection system using a polarizing plate.

FIG. 9 is the view showing an example of the detection system using the polarizing plate.

The detection system using the polarizing plate essentially consists of cylinder mechanism 70, polarizing plates 71, 72, the lens 53, and a light-receiving device 43. The cylinder mechanism 70 moves the polarizing plates 71, 72.

In the case of detection using the polarizing plates, the scattered light generated after the luminous fluxes 111, 112 were irradiated on the film-coated inspection subject 2 is received by the light-receiving device 43 via the polarizing plate 72 and the lens 53. Then, the light reception signal is formed for each polarization component.

As described, influence that the film thickness of the transmissive film of the film-coated wafer, which is given to the detection sensitivity for the inspection subject, is restricted, and the surface inspection of the film-coated wafer can be performed with stable sensitivity, similar to the foregoing example.

According to the present invention, when the film thickness is associated with the detection sensitivity like the transmissive film of the film-coated wafer, the luminous fluxes having a plurality of wavelengths are made incident coaxially on the surface of the film-coated inspection subject, and thus the detection sensitivity can be maintained at a constant level while the influence such as interference due to the difference of film thickness, which occurs on the surface of the film-coated inspection subject, is restricted.

According to the present invention, the influence that the film thickness of the transmissive film of the film-coated inspection subject, which is given to the detection sensitivity for the inspection subject such as particles and flaws, is restricted, and the surface inspection of the film-coated inspection subject can be performed with stable sensitivity.

What is claimed is:

1. A surface inspection apparatus, comprising:
   a light source section that emits a first luminous flux and a second luminous flux;
   an irradiation optical system that irradiates the first luminous flux and the second luminous flux on a surface of a film-coated inspection subject;
   a displacement section that relatively displaces the film-coated inspection subject and an irradiation luminous flux from the irradiation optical system;
   a light-receiving optical system that receives scattered light generated from the inspection subject on the film-coated inspection subject after irradiation of the first luminous flux from the irradiation optical system and scattered light generated from the inspection subject on the film-coated inspection subject after irradiation of the second luminous flux from the irradiation optical system;
   a first light-receiving section that transforms the scattered light of the first luminous flux received by the light-receiving optical system into a first light reception signal;
   a second light-receiving section that transforms the scattered light of the second luminous flux received by the light-receiving optical system into a second light reception signal; and
   a sensitivity stabilizing section that synthesizes the first light reception signal and the second light reception signal to form a signal for sampling, the sensitivity stabilizing section being configured to select a signal having a wavelength for large reflectivity by considering a film thickness of the film-coated inspection subject so that sensitivity is prevented from becoming unstable due to changes of the film thickness.

2. The surface inspection apparatus according to claim 1, wherein a first characteristic of the first luminous flux emitted from the light source section and a second characteristic of the second luminous flux emitted from the light source section are any one of wavelength and polarization component of the luminous fluxes.

3. The surface inspection apparatus according to claim 1, wherein the sensitivity stabilizing section selects either one light reception signal of the first light reception signal and the second light reception signal for every inspection position of the film-coated inspection subject surface, and thus synthesizes the first light reception signal and the second light reception signal.

4. The surface inspection apparatus according to claim 1, wherein the sensitivity stabilizing section selects a light reception signal from which a detection sensitivity closer to desired detection sensitivity has been obtained out of the first light reception signal and the second light reception signal for every inspection position of the film-coated inspection subject surface, and thus synthesizes the first light reception signal and the second light reception signal.

5. The surface inspection apparatus according to claim 1, wherein the sensitivity stabilizing section selects a light reception signal from which higher sensitivity has been obtained out of the first light reception signal and the second light reception signal for every inspection position of the film-coated inspection subject surface, and thus synthesizes the first light reception signal and the second light reception signal.

6. The surface inspection apparatus according to claim 1, wherein a combination of the first luminous flux having the first characteristic and the second luminous flux having the second characteristic is a combination of luminous fluxes such that any one of the first light reception signal and the second light reception signal is obtained with predetermined detection sensitivity for every inspection position of the film-coated inspection subject surface.

7. A surface inspection apparatus, comprising:
a first light source section that emits a first luminous flux;
a second light source section that emits a second luminous flux having different wavelength and/or polarization component from the first luminous flux;
an irradiation optical system that irradiates the first luminous flux with a first incident angle and the second luminous flux with an incident angle different from the first incident angle on a surface of a film-coated inspection subject;
a displacement section that relatively displaces the film-coated inspection subject and an irradiation luminous flux from the irradiation optical system;
a light-receiving optical system that receives scattered light generated from the inspection subject on the film-coated inspection subject after irradiation of the first luminous flux from the irradiation optical system and scattered light generated from the inspection subject on the film-coated inspection subject after irradiation of the second luminous flux from the irradiation optical system;
a first light-receiving section that transforms the scattered light of the first luminous flux received by the light-receiving optical system into a first light reception signal;
a second light-receiving section that transforms the scattered light of the second luminous flux received by the light-receiving optical system into a second light reception signal; and
a detection signal forming section that synthesizes the first light reception signal and the second light reception signal to form a signal for sampling, the detection signal forming section being configured to select a signal having a wavelength for large reflectivity by considering a film thickness of the film-coated inspection subject so that sensitivity is prevented from becoming unstable due to changes of the film thickness.

8. The surface inspection apparatus according to claim 7, wherein the detection signal forming section selects either one light reception signal of the first light reception signal and the second light reception signal for every inspection position of the film-coated inspection subject surface, and thus synthesizes the first light reception signal and the second light reception signal.

9. The surface inspection apparatus according to claim 7, wherein the detection signal forming section selects a light reception signal from which detection sensitivity closer to desired detection sensitivity has been obtained out of the first light reception signal and the second light reception signal for every inspection position of the film-coated inspection subject surface, and thus synthesizes the first light reception signal and the second light reception signal.

10. The surface inspection apparatus according to claim 7, wherein the detection signal forming section selects a light reception signal from which higher sensitivity has been obtained out of the first light reception signal and the second light reception signal for every inspection position of the film-coated inspection subject surface, and thus synthesizes the first light reception signal and the second light reception signal.

11. The surface inspection apparatus according to claim 7, wherein a combination of the first luminous flux having the first characteristic and the second luminous flux having the second characteristic is a combination of luminous fluxes such that any one of the first light reception signal and the second light reception signal is obtained with a predetermined detection sensitivity for every inspection position of the film-coated inspection subject surface.

* * * * *